United States Patent [19]
Repke et al.

[11] 4,193,404
[45] Mar. 18, 1980

[54] STRETCHABLE AND CONFORMABLE PAD

[75] Inventors: Virginia L. Repke, Oak Forest; Robert C. Shepherd, Oak Lawn, both of Ill.

[73] Assignee: Johnson & Johnson, New Brunswick, N.J.

[21] Appl. No.: 896,841

[22] Filed: Apr. 17, 1978

Related U.S. Application Data

[63] Continuation-in-part of Ser. No. 725,764, Sep. 23, 1976, abandoned.

[51] Int. Cl.² ............................................. A61M 1/00
[52] U.S. Cl. ..................................................... 128/280
[58] Field of Search ................... 128/280, 282, 290 R, 128/296, 156, 478, 481, 461, 516

[56] References Cited

U.S. PATENT DOCUMENTS

| | | | |
|---|---|---|---|
| 1,300,212 | 4/1919 | Epp | 128/461 |
| 2,141,408 | 12/1938 | Rosenthal | 128/280 |
| 2,156,512 | 5/1939 | Pitcher | 128/280 |
| 2,891,544 | 6/1959 | London | 128/280 |
| 2,896,623 | 7/1959 | Fitzgerald | 128/280 |
| 3,262,451 | 7/1966 | Morse | 128/290 R |
| 3,356,090 | 12/1967 | Plantinga et al. | 128/280 |
| 3,416,526 | 12/1968 | Yeremian | 128/296 |
| 3,442,268 | 5/1969 | Bird | 128/280 |
| 3,545,442 | 12/1970 | Wicker et al. | 128/296 |
| 3,882,871 | 5/1975 | Taniguchi | 128/287 |
| 4,125,114 | 5/1977 | Repke | 128/280 |

*Primary Examiner*—Robert W. Michell
*Assistant Examiner*—Michael H. Thaler
*Attorney, Agent, or Firm*—Robert L. Minier

[57] ABSTRACT

A disposable nursing pad is provided which comprises a flat but stretchable and conformable body constructed of a plurality of substantially coextensive layers and having a fibrous facing layer, an absorbent inner layer and a moisture-impervious backing layer. The coextensive layers may be constructed of compressively shrunk fabrics. The several layers of the pad are secured together at a plurality of circumferentially spaced zones by means of solidified, flexible strands of resin containing fibers therein, introduced by liquid stitching; or by sonically welding the layers of the pad together at the spaced zones.

23 Claims, 11 Drawing Figures

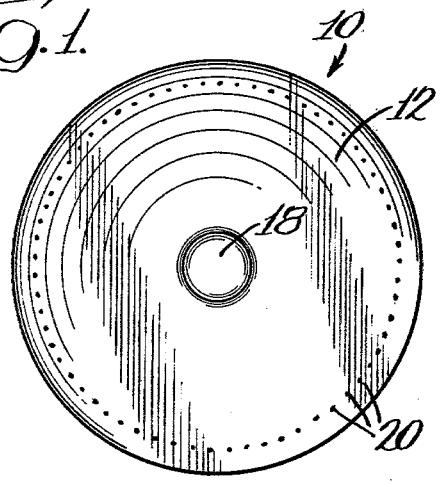
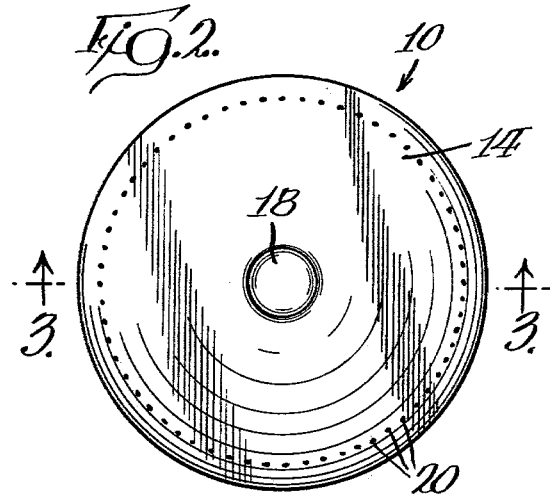
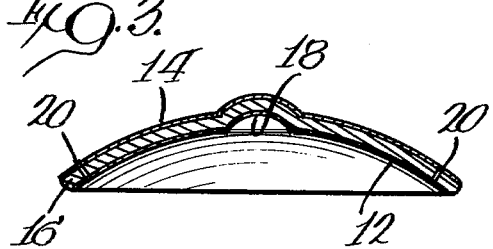
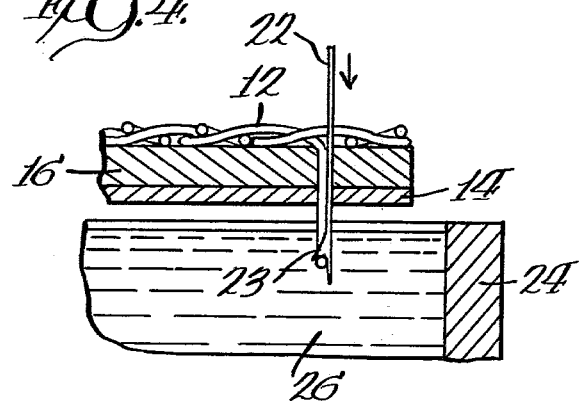
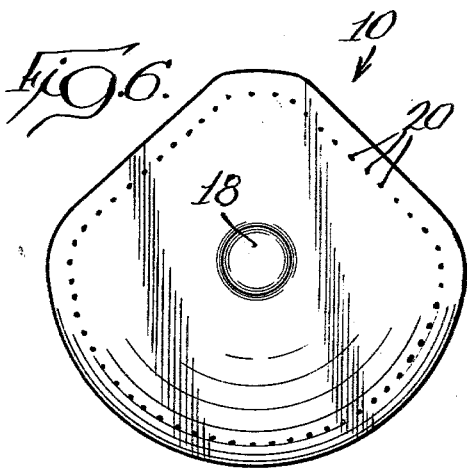
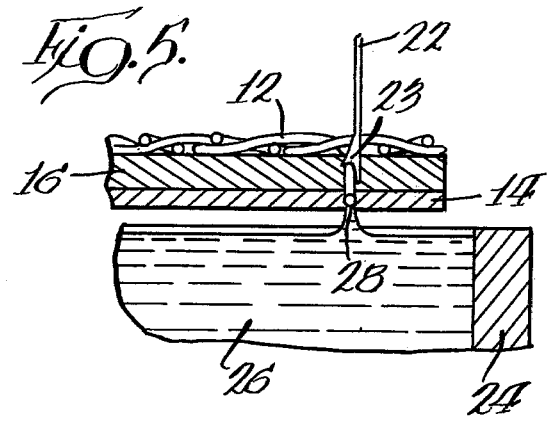

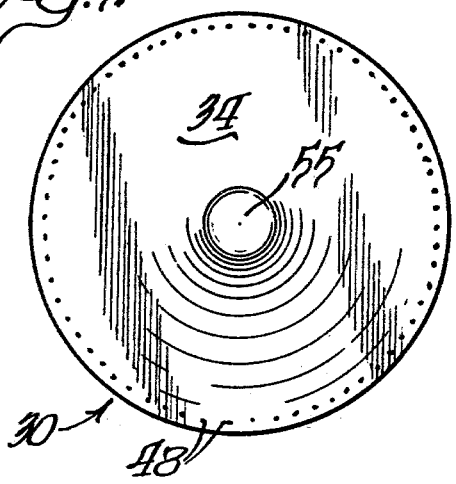
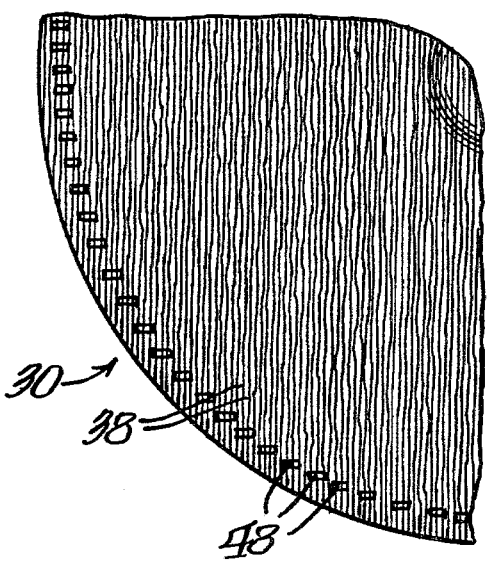
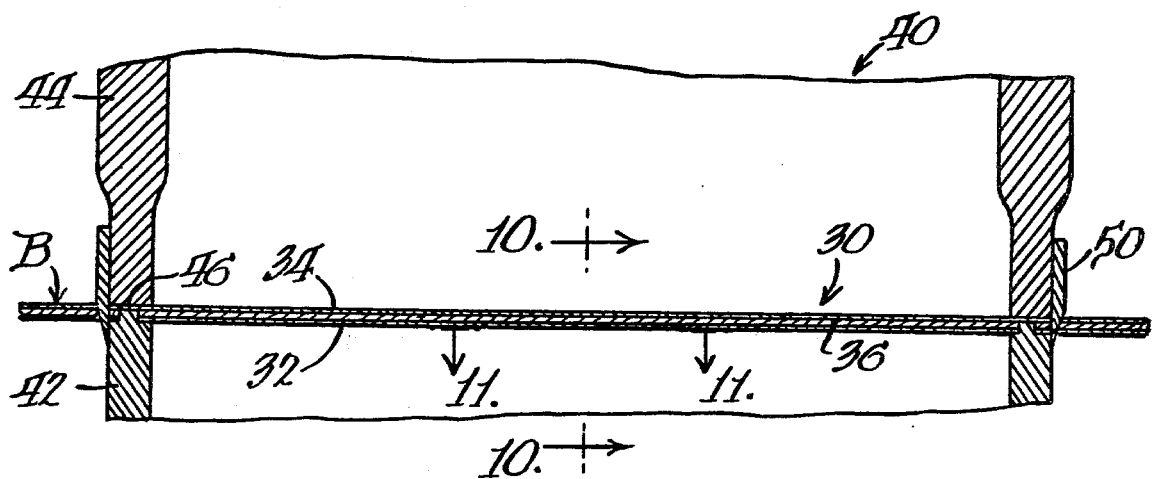
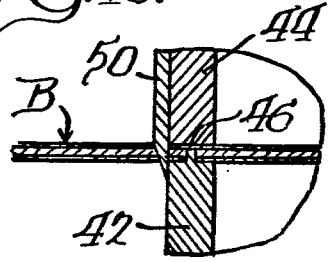
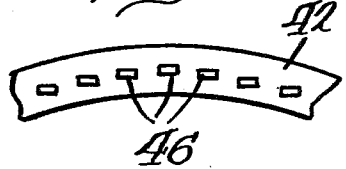

4,193,404

STRETCHABLE AND CONFORMABLE PAD

CROSS REFERENCE TO RELATED APPLICATION

This application is a continuation-in-part of abandoned application Ser. No. 725,764 filed Sept. 23, 1976.

BACKGROUND OF THE INVENTION

Disposable nursing pads are widely used by nursing mothers to minimize and hopefully prevent strike-through of milk onto their clothing. Nursing pads generally comprise several tissue layers stitched together with an absorbent layer across the absorbent area. Typical such nursing pads are shown in U.S. Pat. Nos. 2,869,623 and 2,891,544.

However, the presently available nursing pads suffer from a number of disadvantages. One of the disadvantages of the prior art pads is the problem of strike-through in the stitching areas. Another problem is that of the undesirable soggy feel to the mother after she has worn the pad for a period of time. Yet another problem is that the nursing pads sometimes disintegrate while being used. A further problem is that the currently available pads are substantially dished or cup-shaped in an attempt to follow the contours of the human breast; however, they are not truly comfortable and lack in comfort to the nursing mother. Thus, there is need for an improved nursing pad which minimizes the strike-through problem, and which enhances the comfort of the nursing mother while in use. The present invention provides such a nursing pad.

SUMMARY OF THE INVENTION

The present invention comtemplates an improved disposable nursing pad which has a generally flat but stretchable and conformable body constructed of a plurality of substantially co-extensive fabric layers having different characteristics: a fibrous, facing layer which can be moisture permeable but non-wettable, an absorbent layer which is preferably a web of pulp and polyester fibers; and a backing layer of moisture-impervious material which can be a fibrous web or a plastic sheet. The pad may be constructed entirely of compressively shrunk fabric layers which have been treated by, for example, creping, rubber belt compressing, compacting in the machine direction, compacting in the cross direction, micropleating, or a combination thereof.

In the preferred embodiment, with fibrous facing layer is micropleated, preferably together with at least a portion of an absorbent batt which forms a part of the underlying absorbent layer, the backing layer is micropleated together with another portion of the absorbent layer, provided the absorbent layer is made of a non-woven material, and the various layers are joined together by a securement means such as individual strands or filaments of a flexible resin, thread treated with a hydrophobic agent, and the like. The several layers of the pad preferably are secured together by solidified, flexible strands of resin containing fibers therein, hereinafter referred to as "liquid stiched", at spaced locations around the perimeter of the pad, which securement means provides a number of advantages insofar as ease of manufacture and prevention of the problem of liquid strike-through in the area of stitching is concerned. Alternatively, the spaced securement zones may be provided by sonic welds. The micropleating provides stretch characteristics so that the nursing pad is readily conformable to the contour of the human breast.

The nursing pad of this invention has a number of advantages over currently available nursing pads. The facing layer provides a soft, dry, conformable layer next to the mother's skin which is by far preferable to the cold, soggy feel presently encountered with the conventional tissue-type nursing pads. Thus the nursing pad of the present invention greatly enhances the comfort of the nursing mother. The nursing pad further prevents strike-through of milk onto the mother's clothing which is a common and distressing problem with currently available nursing pads.

The nursing pad of this invention preferably is held together by solidified, i.e., curved or set, liquid stitches which are produced with a needle or a series of needles having barbs or the like appurtenances located at the tips thereof and capable of liquid retention. The barbs are brought through the nursing pad in such a way that they enter through a fibrous layer and exit into a pool of curable liquid resin composition. As the needles pass through the pad on the way to the liquid resin pool, the barbs catch fibers from the uppermost fibrous layer of the pad assembly and dislocate the fibers downwardly and in the thickness direction of the pad assembly. During the return stroke, the needles carry skeins or liquid filaments of resin composition from the pool into the pad assembly. As the needles are drawn back through the nursing pad assembly, the barbs on the tips of the needles wipe the liquid resin on the plurality of layers of the nursing pad through which the needles pass. The liquid resin is subsequently set or cured, thereby sealing the stitching holes as well as securing the plurality of layers together.

Alternatively, the nursing pad may be secured together by a plurality of interfiber welds spaced circumferentially from one another about the perimeter of the pad. Such welds may be created by the application of sonic energy to the nursing pad, and to this end, one or more layers of the nursing pad is provided with thermoplastic fibers in an amount and distribution such that the thermoplastic fibers heat soften, or melt, upon application of sonic energy and fuse to themselves and/or other non-thermoplastic fibers in the layers of the pad thereby creating bonded zones which retain the layers of the nursing pad together.

BRIEF DESCRIPTION OF THE DRAWINGS

In the drawings:

FIG. 1 is a bottom view of the nursing pad of this invention;

FIG. 2 is a top view of the nursing pad of this invention;

FIG. 3 is a cross-sectional view taken along plane 3—3 in FIG. 2;

FIG. 4 is a sectional view of a portion of the nursing pad during the first stage of liquid stitching;

FIG. 5 is a sectional view of the second stage of liquid stitching while manufacturing a nursing pad embodying this invention;

FIG. 6 is a top view of a further embodiment of a pad in accordance with this invention;

FIG. 7 is a top plan view of still another embodiment of a pad in accordance with this invention;

FIG. 8 is an enlarged fragmentary top plan view of the pad of FIG. 7;

FIG. 9 is an enlarged cross-sectional view through an apparatus for sonically sealing the pad of FIG. 7;

FIG. 10 is a cross-sectional view taken generally along plane 10—10 of FIG. 9; and FIG. 11 is a fragmentary plan view taken generally along plane 11—11 of FIG. 9.

DETAILED DESCRIPTION OF THE PREFERRED EMBODIMENTS

The nursing pad of this invention is generally flat, although it can be shaped, such as cupped or dished, if desired. Because of the extensibility of the pad achieved by compressively shrinking or compacting the various layers of the pad, separately or in groups, the nursing pad readily conforms to the contour of the mother's breast.

Once the nursing pad is placed within a brassiere the facing layer of the pad defines an inner concave surface. The backing layer defines an outer convex surface which contacts the inner surface of the brassiere and can be either a repellent-treated fabric web, a plastic sheet or both. The absorbent layer is disposed between the facing layer and the backing layer and serves to absorb and retain moisture.

If the facing layer has been treated or constructed from a hydrophobic fiber web, it can provide an inherently moisture-permeable, non-wettable facing which allows fluid to pass through but remains relatively dry, thereby enhancing comfort to the wearer. The absorbent layer wicks the mother's milk away from the facing layer. Compressive shrinking by micropleating of a ply of the absorbent layer with the facing material further enhances liquid transport by providing intimate contact between adjacent layers which make up the pad assembly. The fluid impervious layer of the nursing pad, which serves as the backing layer, prevents the milk wicked away from the facing layer and retained by the absorbent layer from striking-through onto the mother's clothing.

Several types of fibrous facing materials may be used for the facing layer. Preferable are non-woven polyester fabrics having fabric weights in the range of about 0.5 to 1.5 oz./yd.$^2$ prior to compressive shrinking and containing at least 50% polyester fibers, such as the 50-50 polyester-rayon blend disclosed in U.S. Pat. No. 3,815,602. However, any non-woven fibrous fabric web may be utilized so long as sufficiently long discrete fibers are present which can be utilized in the production of liquid stitches as will be described in detail hereinbelow.

Turning now to the absorbent layer, while a number of suitable materials can be utilized, the absorbent layer is preferably constructed of a wood pulp and polyester fiber blend. Generally speaking, it it preferred to utilize blends containing at least about 10-25% by weight polyester fibers for several reasons. The presence of relatively longer polyester fibers in the absorbent layer makes available additional fibers which are suitable for the liquid stitching process, discussed in detail hereinbelow, and further enhances heat setting of a compressively shrunk absorbent web.

The backing layer is preferably a moisture-repellent, stabilized pulp fabric which has been treated in a conventional manner to provide a liquid barrier. A stretch film of heat sealable thermoplastic film such as an opaque polyethylene web about 0.001" thick or a polyethylene terephthalate web having a thickness of about 0.0005" may alternatively be employed as the backing layer or may be utilized in addition to the stabilized pulp fabric backing layer.

In order to provide stretch and comformability to the nursing pad of this invention, the fabric webs used in the construction of the pad are compressively shrunk, preferably micropleated. The micropleating can be conveniently accomplished prior to the assembly of the web sandwich from which the nursing pad blanks are ultimately cut. Preferably, the facing layer is micropleated together with a portion of the absorbent layer, i.e., together with the adjacent ply or plies of the absorbent layer. Similarly, if the backing layer is a non-woven web, the backing layer can also be micropleated together with an adjacent portion of the absorbent web. It is preferred to employ a web of the same approximate weight for each ply of an absorbent panel and to micropleat one such web together with the facing layer and another such web together with a backing layer. If the backing layer is a stretch film or a heat-sealable thermoplastic film, the second web of absorbent material is preferably micropleated separately. The webs, or groups of webs which make up the pad assembly, can be micropleated according to the method and on an apparatus such as disclosed in U.S. Pat. No. 3,390,218 to Painter et al. and U.S. Pat. No. 3,556,921 to Painter et al.

Non-woven fabric webs that have been compressively shrunk by micropleating can be characterized as an extensible fabric or fabric laminate mechanically compressed along its axis of primary extension. The extensible fabric has a plurality of discontinuous pleats across the width of the fabric which pleats are made up of relatively smaller pleats interrupted in the transverse direction of the fabric by relatively larger pleats. A pleat pattern of relatively smaller and relatively larger pleats extend across the fabric width, each of the relatively larger pleats having adjacent thereto a relatively smaller pleat both in the longitudinal and in the transverse directions. Stated in another way, each relatively larger pleat is separated from nearest pleat of substantially the same size by a relatively smaller pleat.

The aforedescribed micropleated layer composites, e.g., the facing layer plus one or more plies of the absorbent layer, or the backing layer plus one or more plies of the absorbent layer, exhibit the foregoing pleat pattern and additionally have intimate contact between adjacent surfaces of non-woven webs having different density, thickness, fabric weight and fiber composition. In the micropleated fabric laminates the pleats. of one layer having a certain predetermined web composition nest in the pleats of an adjacent layer having a different predetermined web composition.

After the micropleated layer composites or laminates have been superimposed and blanks cut therefrom, the layers of the pads are secured to one another by liquid stitching. The superimposed layer composites are oriented on a liquid stitching device so that a fibrous layer having relatively long fibers, i.e., longer than about $\frac{3}{8}$ inch, preferably about $\frac{1}{2}$ inch and longer, is preferably the upper-most layer. A plurality of needles, preferably barbed or ridged, are disposed around the periphery of a movable needle head having a needle receiving surface adapted to receive a plurality of needles so that the needle configuration conforms to the shape of the periphery of the nursing pad. The needle assembly is moved downwardly so that the needles pass through the various layers of the nursing pad and into a pool of curable or settable liquid resin. As the needles move downwardly, penetrate the nursing pad assembly and ultimately dip into the liquid resin, the barbs or protuberances on the needles catch fibers from the upper fibrous layer or layers and carry the fibers downwardly into the nursing pad assembly. The dislocated fibers may or may not project beyond the lowermost pad layer, depending on the length thereof. As the needle assembly is moved upwardly, the needles carry the resin into the needle holes, thereby sealing the holes created during the stitching operation and also, as the resin is cured or set, embedding within the resin composition the fibers from the upper fibrous layer or layers which have been displaced in the thickness direction.

Suitable liquid resin compositions that can be used for this purpose are dispersions of a synthetic thermoplastic resin in a plasticizer. As additional components, fillers, stabilizing agents, coloring agents, or the like, can also be present. The dispersions usually are relatively thick, viscous pastes which become liquid at elevated temperatures but which, upon curing or setting, produce flexible solid strands. Upon heating, the plasticizer diffuses throughout the thermoplastic resin particles so as to transform the dispersion, upon solidification, from a viscous liquid to an elastomeric or rubber-like material. Such dispersions are usually referred to as plastisols.

Illustrative resins which are suitable for the purposes of the present invention are poly(vinyl chloride), poly(vinyl acetate), copolymers of vinyl chloride and vinylidene chloride, copolymers of vinyl chloride and vinyl acetate, copolymers of vinyl chloride and ethyl maleate, ethylene-vinyl acetate-vinyl chloride terpolymers, mixtures of the foregoing, and the like. Suitable plasticizers for the above resins are tricresyl phosphate, tributyl citrate, dioctyl phthalate, the glycollic acid esters, esters and polyesters of azelaic, adipic, sebacic, benzoic, isobutyric, phosphoric, phthalic and pelargonic acids with $C_8$ to $C_{10}$ branched alcohols, and the like.

The relative amounts of resin and plasticizer can vary, depending on the desired viscosity of the liquid resin composition during the stitching process. Usually about 60 to about 80 parts by weight of plasticizers are compounded with about 20 to about 30 parts by weight of resin; preferably about 70 parts by weight of plasticizer are used for about 30 parts by weight of the resin to produce a plastisol of the desired viscosity.

A particularly preferred plastisol for the present purposes comprises about 70 parts by weight tricrescyl phosphate and about 30 parts by weight of emulsion-polymerized poly(vinyl chloride) having an average particle size of about 2 microns, commercially available under the designation QYNV from Union Carbide Corporation, New York, New York.

After the liquid stitching operation has been completed, the resin introduced into the pads is set or cured into flexible strands of resin. This latter step is usually accomplished by heating the stitched portion of the pad to a temperature of about 250° F. to about 350° F., usually by placing the stitched pad between heated plates or the like.

Instead of the aforedescribed "liquid stitching" technique, the layers of the pads of the present invention may be secured together by sonic sealing. Such a technique eliminates the need for application of a separate adhesive, while at the same time permitting the layers of the pad to be held together at a plurality of spaced securement zones, thereby producing a pad having improved comfort and feel. To permit the pad to be sonically sealed, at least one of the pad layers contains a sufficient amount of thermoplastic fibers to produce interfiber joinder upon the application of sonic energy from a commercially available sonic welding apparatus. In a pad construction where one or more of the pad layers includes a micropleated fabric, the securement zones are provided by short weld segments disposed generally perpendicularly with respect to the length of the micropleats.

Referring to the drawings, nursing pad 10 has a generally flat but conformable body constructed of a plurality of substantially coextensive layers having different characteristics: a fibrous facing layer 12 which can be treated to be moisture-permeable but non-wettable, an absorbent layer 16 which usually comprises several plies, and a backing layer 14 of moisture-impervious material which can be a fabric web or a plastic sheet. The several layers of pad 10 are secured to one another by liquid stitching which provides a series of solidified but flexible strands or "stitches" 20 around the periphery of the nursing pad. The fibrous facing layer 12 defines an inner surface of nursing pad 10 which is adapted to contact and conform to the contour of the breast. Absorbent layer 16 is substantially coextensive with the facing layer. The moisture-impermeable backing layer 14 overlies the the absorbent layer and is substantially coextensive therewith.

As illustrated by FIGS. 1, 2 and 6, nursing pad 10 can be either round or substantially teardrop shaped. As shown in FIG. 3, nursing pad 10 can additionally include a nipple depression such as concavity 18. The nipple depression need not be centered and may, for example, be displaced upwardly from the position shown in FIG. 6 to provide a greater liquid holding capacity at the lower portion of the pad where liquid would tend to wick.

One of the features of nursing pad 10 is its conforability which enables the nursing mother to conform the pad to the shape of the breast. In order to provide stretch and conformability to a nursing pad, the fabric webs used in the construction of nursing pad 10 are compressively shrunk, preferably by micropleating, prior to the cutting of the nursing pad blanks. Preferably, facing layer 12 is micropleated together with one portion of absorbent layer 16 and, if the backing layer 14 is a non-woven web, the backing layer is micropleated with another portion of the absorbent layer 16, and the individually micropleated subassemblies thereafter are superimposed, and secured to one another.

Nursing pad 10 is constructed, in the preferred embodiment, by micropleating facing layer 12 with a 3-oz. web of absorbent layer 16. A second 3-oz. web of absorbent material is micropleated with the web which is utilized for backing layer 14. The two micropleated webs are then superimposed so that the micropleated absorbent layers face each other and the nursing pad blanks are cut from the web assembly, either in the round or the teardrop shape as shown in FIGS. 1 and 2, or FIG. 6, respectively. Additional fabric economy can be achieved by utilizing the teardrop shape.

Layers 12, 14 and 16 are secured by liquid stitches 20 which are formed as follows. The nursing pad 10 is placed under a needle head (not shown) having a plurality of needles 22 affixed thereto. Each needle 22 has barb 23 at the end or adjacent the end thereof. The needle head is brought down so that it penetrates the unsecured layers of the nursing pad. The unsecured layers are oriented so that the needle 22 first passes through fibrous facing layer 12, then through absorbent layer 16 and finally through the backing layer 14. Needle 22 continues its downwardly passage until it contacts liquid resin pool 26 which is contained in pot 24 located underneath the unsecured layer of pad 10. As needle 22 passes downwardly through facing layer 12 and ultimately dips into the pool of liquid resin, barb 23 catches fiber 28 and dislocates and carries fiber 28 downwardly through absorbent layer 16 and backing layer 14. If desired, the cutting step and the liquid stitching step can be performed simultaneously by appropriately mounting the cutting means onto the needle head.

Turning now to FIG. 5, when needle 22 is moved upwardly and travels through backing layer 14, absorbent layer 16 and facing layer 12, barb 23 pulls the liquid resin skein through the hole made by needle 22 when it first penetrated the three layers while dislocated fiber 28 remains dislocated and extending in the transverse direction. Fiber 28 together with the introduced liquid resin serve to seal the needle hole once the resin cures and assure that there is no leakage of fluid therethrough.

It is to be understood that a needle head having a single needle could be employed and that the holder containing the unsecured layers which form the nursing pad could be rotated below a single reciprocating needle so that individual stitches are made around the periphery of nursing pad 10. The needle-carrying head also could be rotated to achieve the same effect. However, in the preferred embodiment, the needle head has a plurality or bank of needles 22 so that the layers of nursing pad are secured about the periphery thereof in one step.

Nipple depression 18 can be formed during the needling process or in a separate step using an appropriate die form. If a plastic backing layer is to be used, the nipple depression could be formed during a heat sealing step for the plastic layer, if such a step is performed. The plastic layer can also be secured to the nursing pad by liquid stitching at the same time with the various fabric layers thereof.

It is to be understood that while it is preferred to construct a nursing pad wherein each of coextensive layers of the pad are compressively shrunk, it is also contemplated that the facing layer alone, the facing layer and a portion of the absorbent layer, the facing layer and the entire absorbent layer, the backing layer alone, the backing layer and a portion of the absorbent layer or the backing layer and the entire absorbent layer may be compressively shrunk to impart the desired stretchability and conformability to the nursing pad, depending upon the nature of each of fabric webs utilized in the construction of the pad and the desired degree of stretchability.

As aforementioned, absorbent layer 16 preferably includes at least some thermoplastic fibers, eg., polyester fibers. In this regard, it has been found that an absorbent layer consisting of a blend pulp fibers and polyester fibers in an amount of about 5% to about 10%, and up to about 25% by weight, contributes significant stability to the pad for micropleating thereof in accordance with the teachings of the Painter et al. patents mentioned above. Furthermore, the presence of thermoplastic fibers in the absorbent layer contributes to the ability to secure the layers of the pad together by the application of sonic energy, as described in detail below, particularly when the facing and/or backing also contains at least some thermoplastic fibers. In lieu of providing thermoplastic textile length fibers, such as polyester fibers, in the absorbent layer the present invention contemplates that synthetic polymeric fibers of papermaking length may be utilized in the absorbent panel either alone, or in a blend with wood pulp fibers.

Synthetic polymeric fibers that have physical and morphological characteristics generally similar to pulp fibers produced from natural woods have been known for approximately 10 years. Examples of such fibers are the synthetic wood pulp fibers formed of polyethylene that are sold by Crown Zellerbach under the trademark SWP.

Various methods of making synthetic wood pulp fibers are known, including (1) solution polymerization accompanied by stirring, (2) dissolving a preformed polymer and subjecting the solution to an anti-solvent, or (3) forming the polymer at the interface between liquid layers, with localized stirring provided to pull the polymers thus formed into fibrillated forms. Examples of methods of producing synthetic wood pulp fibers are disclosed in U.S. Pat. Nos. 3,560,318; 3,081,519; 3,003,912; 3,068,527; and 3,290,207; South African Pat. No. 697,431; United Kingdom Pat. No. 1,102,342; and Netherlands patent application No. A132/487313178.

As used in this specification and the appended claims, the term "synthetic wood pulp fibers" means synthetic, water dispersible, thermoplastic, elongated, supple, randomly bent, polymeric fibers or fibrils generally similar in size and shape to conventional wood pulp fibers produced from naturally occuring woods. Each "synthetic wood pulp fiber" is of irregular cross sectional shape measured at any given point along its length, and in addition is nonuniform in cross section along its length. The predominant shape of the fibers is usually rather ribbon-like.

Referring now to FIGS. 7–11, a nursing pad 30 is illustrated therein which has the same general construction as previously described nursing pad 10. To this end, nursing pad 30 includes a facing layer 32 adapted to be positioned against the mother's breast, a coextensive intermediate absorbent layer 36, and a coextensive outer or backing layer 34.

Facing layer 32 is a moisture permeable non-wettable fabric of the type described above which is mechanically compacted to provide parallel micropleats 38, which extend from top to bottom of the pad, as viewed in FIG. 8. As is noted above, at least a portion of the absorbent layer 36 may be micropleated along with facing layer 34. And, as is also explained above, backing layer 32 is a moisture-impervious member, or a fabric which is treated to be generally moisture-impervious. Backing layer 32 may also be micropleated (alone or together with at least a portion of the absorbent layer), and such micropleats are parallel to micropleats 38.

Nursing pad 30 is preferably formed from a blank B of laminated plies that are secured together in a sonic welding apparatus shown generally at 40 in FIG. 9. Apparatus 40 may be of the type that is commercially available from Branson Instruments, Incorporated of Stanford, Connecticut and sold under Model No. 460. Such apparatus may include an annular anvil 42 and an annular horn 44 that are disposed in vertical reciprocal relationship with respect to one another to permit blank B to be fed therebetween. When blank B is in position, relative movement is effected between the anvil and horn to clamp blank B therebetween, and horn 44 is energized to transmit vibrations in the ultrasonic frequency range into the blank.

Anvil 42 includes a plurality of circumferentially spaced raised land areas 46 disposed about the upper surface thereof. Land areas 46 are each of generally the same size and shape, and in the illustrated embodiment land areas 46 are generally rectangular, parallel to one another, and disposed perpendicularly with respect to the length of micropleats 38. It has been found that a nursing pad that is sonically sealed with an apparatus of the type described above includes a plurality of generally rectangular, circumferentially spaced securement zones 48 disposed about the periphery of the pad and spaced slightly inwardly of the marginal edge thereof, as can be best seen in FIG. 8. The securement zones, or welds, serve to retain the pad 30 together by virtue of the sonically induced heat softening, or melting of the thermoplastic fibers in the facing, and/or absorbent, and/or backing layers. The sonically induced welds are spaced inwardly (depthwise) of the outer layer of the pad to produce a product that not only has a pleasing appearance, but which also is very comfortable to the mother, since the weld zones are recessed inwardly of the pad, and only the soft comfortable facing fabric contacts the mother's skin.

Individual pad 30 may be severed from the blank B simultaneously with the sonic sealing operation by an annular blade 50 projecting below horn 44 and moveable into blank severing relationship with blank B when the horn and anvil are reciprocated relative to one another.

Nipple depression 55 may be formed simultaneously with the sonic sealing and pad severing step, or in a separate operation.

It should be understood that while an annular anvil and horn have been illustrated, the present invention is not limited thereto and other sonic sealing devices, such as rolls, wheels etc. may be used in place thereof, as will occur to those skilled in the art. And, a mass of pressure adhesive may be provided on the backing or facing layer for adhering the pad to the inside of a brassiere, or to the mother's skin if it is desired to positively hold the pad in place.

The foregoing discussion and the drawings are intended as illustrative and are not to be taken as limiting. Still other variations are possible without departing from the spirit and scope of this invention.

We claim:

1. A disposable nursing pad in the form of a stretchable and conformable body having an inner surface adapted to conform to the contour of a human breast and an outer surface adapted to be received within a brassiere which comprises a fibrous, fabric facing layer defining said inner surface, an absorbent layer substantially coextensive with said facing layer, a moisture-impermeable backing overlying said absorbent layer, and securement means for binding said facing layer, said absorbent layer and said backing layer forming a unitary pad, at least one of said layers being constructed from an extensible compressively shrunk fabric web providing stretchability and conformability, said securement means being defined by a plurality of securement zones spaced from one another circumferentially about the periphery of the pad.

2. The disposable nursing pad of claim 1 wherein said securement means comprises solidified flexible strands of resin containing fibers embedded therein.

3. The disposable nursing pad of claim 2 wherein each of the layers is a compressively shrunk web.

4. The disposable nursing pad of claim 1 wherein each of the layers is a compressively shrunk web.

5. The disposable nursing pad of claim 1 wherein said facing layer prior to compressive shrinking has a fabric weight of about 0.5 to about 1.5 oz./yd$^2$.

6. The disposable nursing pad of claim 1 wherein said body is substantially round in shape.

7. The disposable nursing pad of claim 1 wherein said body is substantially of a teardrop shape.

8. The disposable nursing pad of claim 1 wherein said backing layer and at least a portion of said absorbent layer together form a compressively shrunk laminate.

9. The disposable nursing pad of claim 1 wherein said facing layer and at least a portion of said absorbent layer together form a compressively shrunk laminate.

10. The disposable nursing pad of claim 1 wherein said facing layer is a micropleated fabric web.

11. The disposable nursing pad of claim 1 wherein said facing layer and at least a part of said absorbent layer together form a micropleated laminate.

12. The disposable nursing pad of claim 1 wherein said facing layer, said absorbent layer, said backing layer are micropleated webs, and wherein a portion of said absorbent layer forms a laminate with said facing layer and the remainder of the absorbent layer forms a laminate with said backing layer.

13. The disposable nursing pad of claim 1 wherein said facing layer is a micropleated polyester fabric web.

14. The disposable nursing pad of claim 1 wherein at least one of said layers includes at least some thermoplastic fibers, and wherein said securement means comprises weld zones created by the application of sonic energy.

15. The disposable nursing pad of claim 14 wherein at least one of said layers is micropleated, and wherein said zones are generally rectangular in shape and disposed generally perpendicularly with respect to the length of said micropleats.

16. The disposable nursing pad of claim 14 wherein said absorbent layer includes at least some wood pulp fibers and at least some synthetic wood pulp fibers.

17. A disposable nursing pad in the form of a flat but conformable body having an inner surface adapted to conform to the contour of a human breast and an outer surface adapted to be received within a brassiere which comprises a micropleated polyester fabric facing layer defining said inner surface, an absorbent layer substantially coextensive with said facing layer, a moisture-impermeable backing overlying said absorbent layer, and securement means for binding said facing layer, said absorbent layer and said backing layer to form a unitary pad, said absorbent layer and said backing layer being micropleated so as to impart additional conformity to said body, said securement means being defined by a plurality of securement zones spaced from one another circumferentially about the periphery of the pad.

18. The disposable nursing pad of claim 17 wherein said securement means comprises solidified flexible strands of resin containing fibers embedded therein.

19. The disposable nursing pad of claim 17 wherein said body is in a teardrop shape.

20. The disposable nursing pad of claim 17 wherein said body is substantially round in shape.

21. The disposable nursing pad of claim 17 wherein at least one of said layers includes at least some thermoplastic fibers, and wherein said securement means comprises weld zones created by the application of sonic energy.

22. The disposable nursing pad of claim 17 wherein at least one of said layers is micropleated, and wherein said zones are generally rectangular in shape and disposed generally perpendicularly with respect to the length of said micropleats.

23. The disposable nursing pad of claim 17 wherein said absorbent layer includes at least some wood pulp fibers and at least some synthetic wood pulp fibers.

* * * * *